(12) United States Patent
Sample et al.

(10) Patent No.: US 8,404,775 B2
(45) Date of Patent: Mar. 26, 2013

(54) METHOD FOR FUNCTIONALIZING NANOTUBES AND IMPROVED POLYMER-NANOTUBE COMPOSITES FORMED USING SAME

(75) Inventors: Jennifer L. Sample, Bethesda, MD (US); Amy A. Hofstra, Greenbelt, MD (US)

(73) Assignee: The Johns Hopkins University, Baltimore, MD (US)

( * ) Notice: Subject to any disclaimer, the term of this patent is extended or adjusted under 35 U.S.C. 154(b) by 8 days.

(21) Appl. No.: 12/946,547

(22) Filed: Nov. 15, 2010

(65) Prior Publication Data

US 2011/0086987 A1   Apr. 14, 2011

Related U.S. Application Data

(63) Continuation of application No. 11/846,672, filed on Aug. 29, 2007, now abandoned.

(51) Int. Cl.
*C08K 3/04* (2006.01)
*C07C 15/60* (2006.01)

(52) U.S. Cl. ........ 524/495; 524/496; 524/847; 585/422; 585/435; 977/742; 977/745; 977/746; 977/748

(58) Field of Classification Search .................. 524/495, 524/496; 977/842
See application file for complete search history.

(56) References Cited

U.S. PATENT DOCUMENTS

| | | | |
|---|---|---|---|
| 6,515,325 B1 | 2/2003 | Farnworth et al. | |
| 6,843,902 B1 | 1/2005 | Penner et al. | |
| 6,905,667 B1* | 6/2005 | Chen et al. | 423/447.1 |
| 6,955,800 B2 | 10/2005 | Resasco et al. | |
| 7,094,386 B2 | 8/2006 | Resasco et al. | |
| 2004/0186220 A1* | 9/2004 | Smalley et al. | 524/548 |
| 2004/0266939 A1* | 12/2004 | Chen et al. | 524/496 |

OTHER PUBLICATIONS

Hedderman, Theresa G., Sinead M. Keogh, Gordon Chambers, and Hugh J. Byrne. (Nov. 13, 2004) Solubilization of SWNTs with Organic Dye Molecules. Journal of Physical Chemistry B (108) pp. 18860-18865. Online at: http://pubs.acs.org/doi/pdf/10.1021/p0491481.*
Moniruzzaman et al. "Polymer Nanocomposites Containing Carbon Nanotubes" American Chemical Society, Jul. 7, 2006,Macromolecules 2006, 39, 5194-5205.
Lou, Xudong et al. "Synthesis of Pyrene-Containing Polymers and Noncovalent Sidewall Functionalization of Multiwalled Carbon Nanotubes", American Chemical Society Sep. 25, 2004, Chem. Mater. 2004, 16, 4005-4011.
Petrov, Petar et al. "Noncovalent Functionalization of Multi-Walled Carbon Nanotubes by Pyrene Containing Polymers" Chem. Commun., 2003, 2904-2905.
Fernando, K.A. Shirai et al. "Diminished Band-Gap Transitions of Single-Walled Carbon Nanotubes in Complexation . . . " J. Am. Chem. Soc. 2004, 126, 10234-102.
Tsubokawa, Norio "Preparation and Properties of Polymer-grafted Carbon Nanotubes and Nanofibers" Polymer Journal, vol. 37, No. 9, pp. 637-655 (2005).
Liu, I-Chun et al. "Preparing a Styrenic Polymer Composite Containing Well-Dispersed Carbon Nanotubes: Anionic . . . " Macromolecules 2004, 37, 283-287.

(Continued)

*Primary Examiner* — Ling Choi
*Assistant Examiner* — Darcy D LaClair Lynx
(74) *Attorney, Agent, or Firm* — Noah J. Hayward

(57) ABSTRACT

A polymerizable ligand comprising, in one embodiment, a polyaromatic compound, with a terminal functional group, non-covalently bonded to the sidewalls of carbon nanotubes. This structure preserves the structural, mechanical, electrical, and electromechanical properties of the CNTs and ensures that an unhindered functional group is available to bond with an extended polymer matrix thereby resulting in an improved polymer-nanotube composite.

18 Claims, 8 Drawing Sheets

OTHER PUBLICATIONS

Yin, Aijun et al. "Postgrowth Processing of Carbon Nanotube Arrays-Enabling New Functionalities and Applications" IEEE Transactions on Nanotechnology, vol. 3, No. 1, Mar. 2004 pp. 147-151.

Curulli, A. et al. "Functionalization and Dispersion in a Polymer-Matrix of Single-Wall Carbon Nanotubes: . . . " 2004 4th IEEE Conference on Nanotechnology pp. 524-526.

* cited by examiner

METHOD FOR FUNCTIONALIZING NANOTUBES AND IMPROVED POLYMER-NANOTUBE COMPOSITES FORMED USING SAME

CROSS-REFERENCE TO RELATED APPLICATIONS

This application is a continuation application of U.S. patent application Ser. No. 11/846,672, filed Aug. 29, 2007, now abandoned, which claims the benefit of prior filed, U.S. provisional application: Ser. No. 60/823,769, filed on Aug. 29, 2006, which is hereby incorporated by reference in its entirety.

STATEMENT OF GOVERNMENTAL INTEREST

This invention was made with Government support under National Aeronautics and Space Administration grant no. NNGO5GR51A. The Government has certain rights in the invention.

BACKGROUND OF THE INVENTION

1. Field of the Invention

The present invention relates generally to functionalizing nanotubes to form improved polymer-nanotube composites and, more particularly, to a method for functionalizing carbon nanotubes with a polymerizable ligand formed using polymerizable groups, for example, vinyl or styryl groups, in combination with a polyaromatic molecule such as a polyaromatic hydrocarbon (PAH) for the purpose of achieving significant improvements in the properties of a polymer-nanotube composite due to improved dispersion and chemical bonding between the polymer matrix and the nanotube itself.

2. Description of Related Art

Sustaining habitation on the moon, or any other planet, will require light weight, high strength structures that protect against both radiation and particulates. Chemical synthesis techniques to enable strong bonding between carbon nanotubes and polymers to form improved polymer-nanotube composites, technology which could be used for this application, are needed.

Polymer properties such as electrical conductivity have been shown to be enhanced by incorporating therein a combination of carbon fibers or carbon nanotubes (CNTs). Additionally, CNTs have been shown to prevent delamination and provide structural stability in polymer composites. Because CNTs have uniquely high strength to mass ratio, intrinsic light weight, thermal conductivity, electrical conductivity, and chemical functionality, and, as noted, have been shown to prevent delamination and provide structural stability in polymer composites, they can impart these properties to polymers when effectively combined therewith.

Though CNTs have extraordinary mechanical properties, their ability to strengthen polymers and epoxies is limited by the strength of interfacial bonding. As a result, when incorporated into polymeric resin without cross-linking or functionalization, they lack the ability to transfer loads across the structure.

CNTs can be functionalized via covalent or non-covalent bonding, to either the ends of the nanotubes or to the sidewalls. Covalent functionalization often requires beginning with modified tubes, such as fluorinated nanotubes, or with purified tubes where defect sites in the CNTs are produced by oxidation. Because these modifications often result in the disruption of the bonds along the tubes themselves, covalent functionalization can degrade the mechanical and electrical properties of the nanotubes and, thus, is not ideal for all applications.

Therefore, the present invention has been made in view of the above problems, and it is an objective of the present invention to provide a method for functionalizing carbon nanotubes using polymerizable ligands and to form improved polymer-nanotube composites utilizing the functionalized nanotubes.

SUMMARY OF THE INVENTION

Non-covalent functionalization to the sidewalls of CNTs can be attained by exploiting the van der Waals and pi-pi bonding between the pi electrons of the CNTs and that of a polyaromatic molecule, for example, a polyaromatic hydrocarbon (PAH) such as anthracene. This type of functionalization results in higher degrees of functionalization as the entire length of the CNT can be functionalized rather than just the ends and specific active sites. Like end-functionalization, non-covalent functionalization also opens up the possibility for tailoring the functionalization via the choice of molecule.

For the purpose of polymerizing the CNT to a polymer resin or epoxy, in one embodiment, a polymerizable ligand comprising a polyaromatic molecule such as PAH with an appropriate polymerizable group such as a vinyl, styryl, or amino group can be non-covalently bonded to the CNTs. In the embodiment shown in FIG. 1, single-walled carbon nanotubes (SWNTs) are functionalized with a polymerizable ligand, vinylanthracene, thereby enabling improved crosslinking or bonding and dispersion of CNTs into a polymer. This results in improving the mechanical properties of the interface between the CNTs and the polymer thereby imparting many of the valuable properties of CNTs into the polymer matrix resulting in a significantly improved polymer-nanotube composite.

BRIEF DESCRIPTION OF THE DRAWINGS

These and other objects, features and advantages of the invention will be apparent from a consideration of the following Detailed Description considered in conjunction with the drawing Figures, in which.

DETAILED DESCRIPTION

Figure 1:
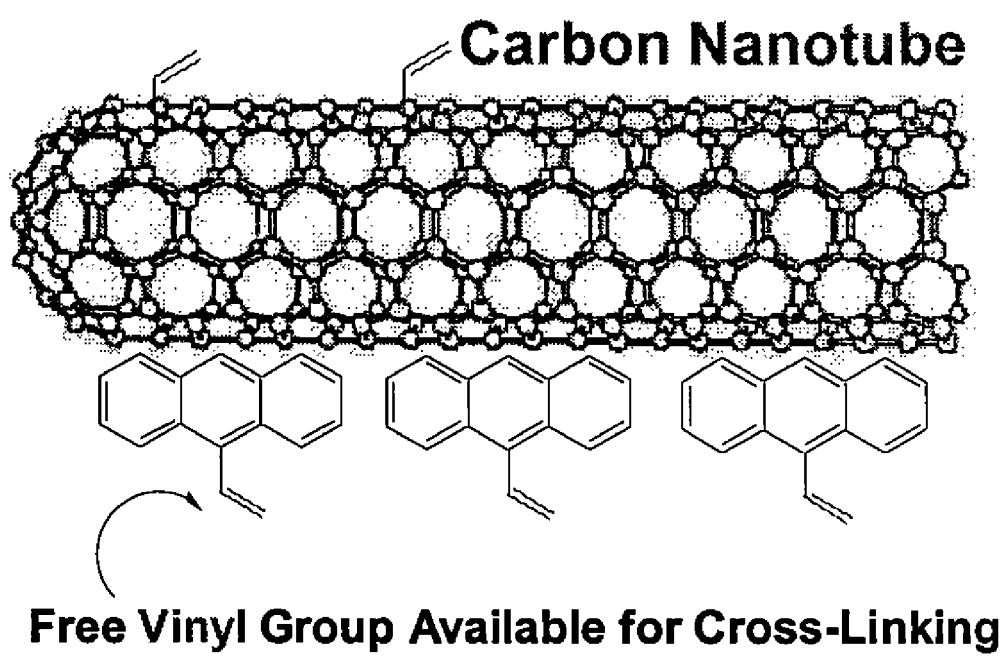
FIG. 1 is a schematic of a SWNT functionalized with vinylanthracene.

In a first set of experiments, the CNTs were SWNTs produced by the HipCO method and purified by refluxing in 3M $HNO_3$ for 16 hours. To functionalized the nanotubes, a mixture of CNTs and vinylanthracene, at a ratio of 1:2 by weight, were sonicated for approximately one hour in dry tetrahydrofuran (THF). To remove unreacted vinylanthracene, CNTs were collected by filtration, washed with THF, and dried over vacuum in air. Absorbance and fluorescence data were collected as evidence of functionalization.

The CNTs in the second set of experiments were MWNTs purified in 3M $HNO_3$ for 4 hours. A shorter reflux time was chosen to preserve longer length tubes. To functionalize the nanotubes, a mixture of CNTs and the appropriate anthracene derivative, at a ratio of 2:5 by weight, were mixed in THF for 72 hours. To remove unreacted ligand, CNTs were collected by filtration, washed with THF, and dried over vacuum in air. Fluorescence data was collected as evidence of functionalization.

In situ synthesis of nylon 12 was completed in solution, based on the Haggenmueller method for nylon 6. A solution of 0.0325 M diaminododecane was prepared by stirring for 24 hours in chloroform, solution A. A solution of dodecanedioyl chloride in toluene was prepared at three times the concentration, 0.0975 M, solution B. To prepare a batch of Nylon 12, 300 mL of Solution A were placed in a 600 mL beaker and stirred with an overhead stirrer at 230 rpm for about one minute. If appropriate, CNTs from above were ground with mortar and pestle, and then added to the beaker. Finally, 100 mL of solution B were added and left to stir for 30 minutes. The nylon produced was collected with a glass frit filter, washed with toluene and chloroform, and dried over vacuum in air. Typical yields were about 85%.

Nylon produced from the in situ methods was analyzed by scanning electron microscope (SEM). The polymer was overcoated with gold to improve the quality of the images recorded. The SEM used was Hitachi S-4700 Cold Field Emission Scanning Electron Microscope (FE-SEM). Images were recorded at 5 kV at short working distances around 5 to 6 mm.

Electronic structure of carbon nanotubes is dominated by van Hove singularities which give rise to distinct peaks in the density of states as seen by I/V measurements. The first electronic transition in metallic carbon nanotubes is denoted $M_{11}$ and the first and second electronic transitions in semiconducting carbon nanotubes are denoted $S_{11}$ and $S_{22}$, respectively. These transitions typically correspond to absorbances in the visible and near infrared wavelengths. Absorption spectra of solution-phase carbon nanotube suspensions typically exhibit all of these features due to the presence of all types of CNTs in solution. Chemical affinity-induced separation of metallic from semiconducting nanotubes via functionalization and centrifugation has been tracked via these resonances, as has chemical doping resulting in disruption of the electronic structure of the CNTs. Changes in these resonances were used to observe changes in electronic structure resulting from functionalization with vinylanthracene.

Figure 2:
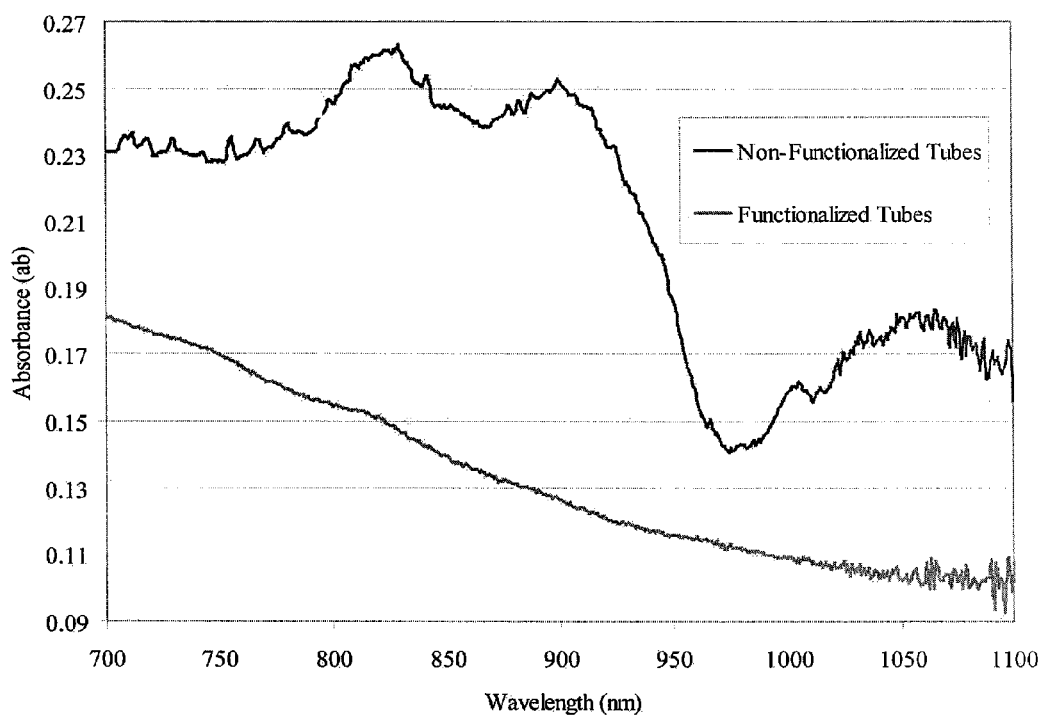
FIG. 2 is a graph illustrating the absorption spectra of SWNT solution before and after functionalization with vinylanthracene.

Surface modification has been shown to affect the $S_{11}$ and $S_{22}$ electronic transitions in carbon nanotubes. A solution having molarity $2 \times 10^{-3}$M of purified unfunctionalized nanotubes (background substracted for 1% wt. Triton X-100 in THF) exhibited broad peaks characteristic of solution-phase $S_{11}$ and $S_{22}$ level transitions. Functionalized nanotube solution exhibited no such peaks within the same range of wavelengths, as shown in FIG. 2. This diminished $S_{11}$ peak intensity after non-covalent functionalization of nanotube sidewalls is known in the literature. It is thought that complexation in this manner may change the electronic density of states of the nanotube. Similarly functionalized SWNTs have been compared to highly defective double-walled nanotubes having significantly different density of states from a pristine SWNT.

Figure 3:
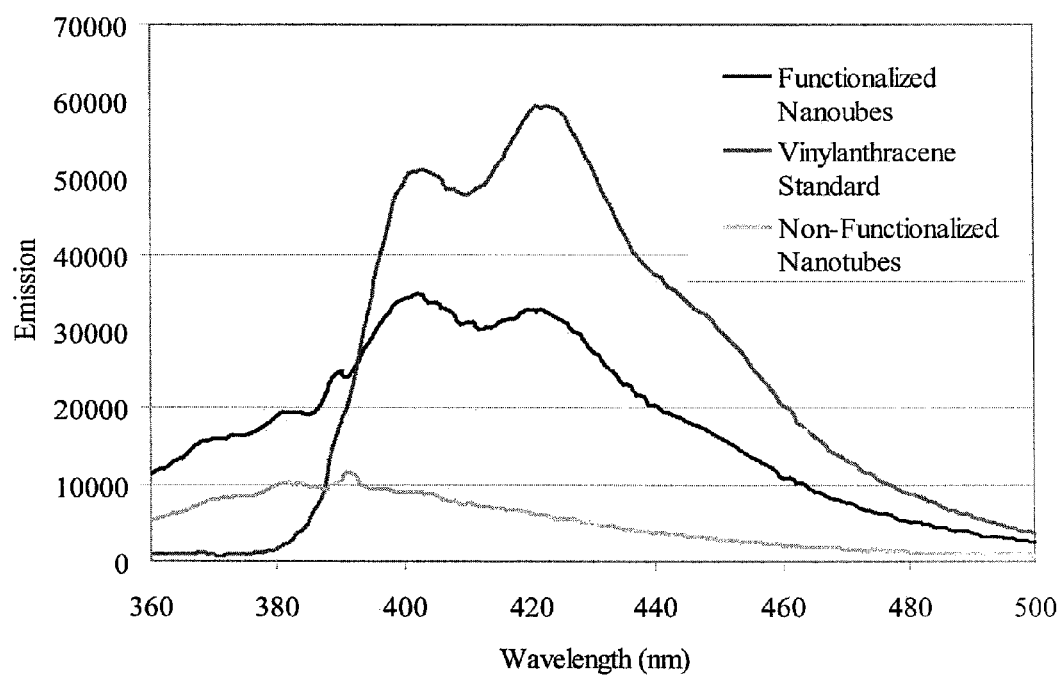
FIG. 3 is a graph illustrating fluorescence spectra of purified SWNTs, vinylanthracene alone, and vinylanthracene functionalized SWNTs.

In addition to changes in the absorption spectra, functionalization of carbon nanotubes can be observed through changes in fluorescence before and after functionalization, particularly when the ligand or attached group is fluorescent. This is the case with vinylanthracene, which fluoresces strongly at ~400-420 nm when excited at 350 nm, as shown in FIG. 3. The SWNTs used in these experiments did not have any overlapping fluorescence in this region, thus the presence of vinylanthracene fluorescence peaks in a well-rinsed and purified functionalized SWNT sample is indicative of functionalization. Fluorescence spectra of purified SWNTs prior to functionalization with vinylanthracene, of vinylanthracene in solution, and of vinylanthracene-functionalized SWNTs are shown in FIG. 3.

Precipitated CNTs were removed from filter paper after washing and suspended in heptane. Heptane was selected because it is a dry solvent that does not have any fluorescent or Raman peaks near those of vinylanthracene. Emission spectrum of this solution and of a $2 \times 10^{-4}$ M standard of vinylanthracene in heptane were recorded. The wavelengths of the fluorescence peaks were very similar in the two cases. Peaks appeared at 404 and 423 nm for the unbound vinylanthracene, and at 403 and 422 nm for the filtrate solution. By contrast, the relative heights of the peaks shifted somewhat; in the standard sample, the peak at 422 nm is higher than that at 403 nm, while the peaks are approximately equal in height for the functionalized CNTs. This difference may be the result of a slight fluorescence quenching due to energy transfer between the bound vinylanthracene and CNT wall.

A series of standards of vinylanthracene were used to create a calibration curve. The estimated concentration of CNT-bound vinylanthracene using this calibration curve is approximately $3.2 \times 10^{-6}$ M. The number of vinylanthracene molecules per SWNT can be computed if the average molecular weight of a carbon nanotube is known. For these calculations, the weight of the CNTs was estimated by assuming an average bond length of 0.32 nm, a tube diameter of 0.7 nm, and tube lengths between 1 and 10 nm. Assuming the average molecular weight of a carbon nanotube is 2,242,800 g/mol, the ratio is roughly estimated to be about 143 molecules of vinylanthracene per nanotube. A similar set of fluorescence experiments was completed to confirm the functionalization of MWNTs with vinylanthracene.

Scanning electron microscopy (SEM) was used to image nylon that was produced by the in situ process in order to determine how well the CNTs were dispersed throughout the polymer. It is critical that the CNTs be well dispersed in order to maximize their effect on the material's mechanical and rheologic properties. If the tubes are clumped together, then large regions of the polymer substrate will insulate the tubes, and the overall thermal and electrical conductivity will be low. In addition, evidence of good dispersion may indicate that the polymer is chemically bonding to the functional groups along the CNTs. It has been suggested that CNTs which are dispersed within a polymer but not chemically bound to it, can rotate or shift, and therefore do not effectively resist strain applied to the material. Creating a physical bond directly between the polymer and the CNTs or its functional groups, should increase the modulus of the bulk material.

Figure 4:
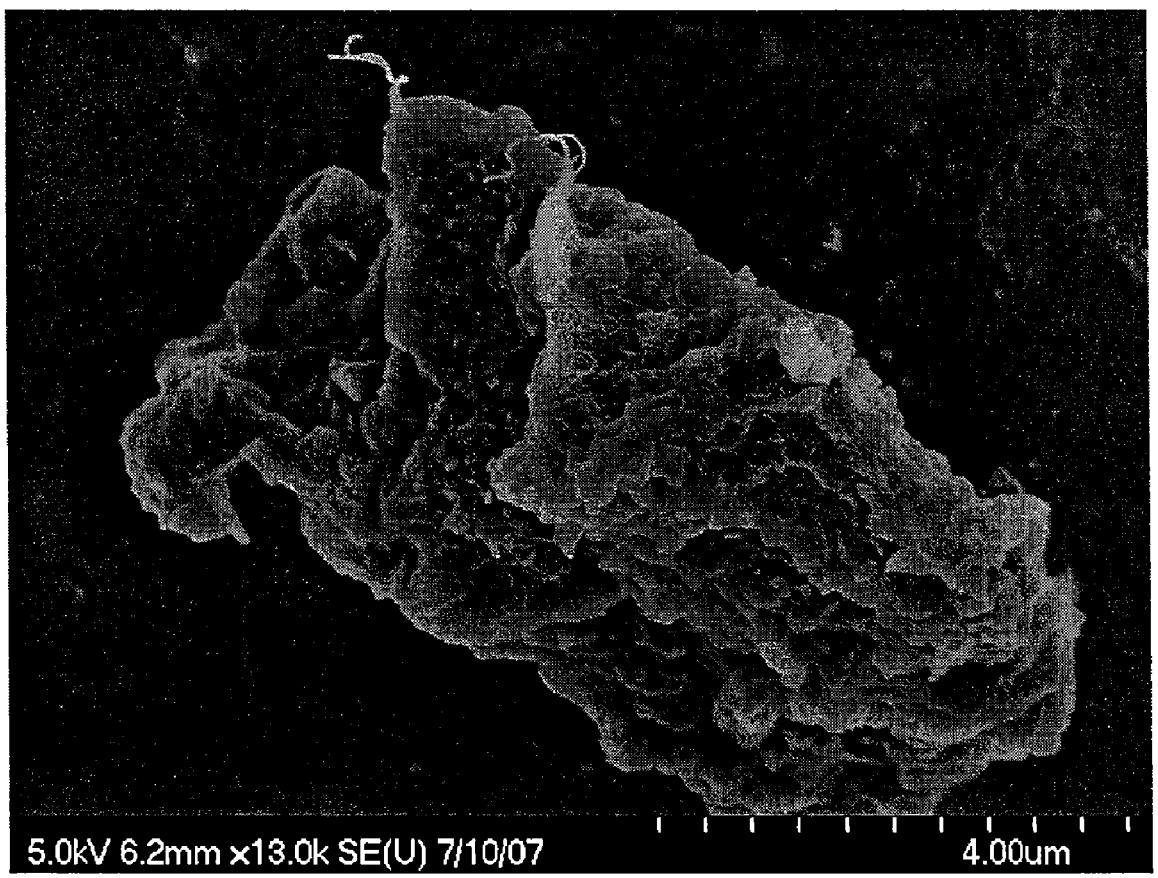
FIG. 4 is a scanning electron microscope (SEM) image of nylon 12 with approximately 1% by weight of purified but non-functionalized multi-walled carbon nanotubes (MWNTs).
Figure 5:
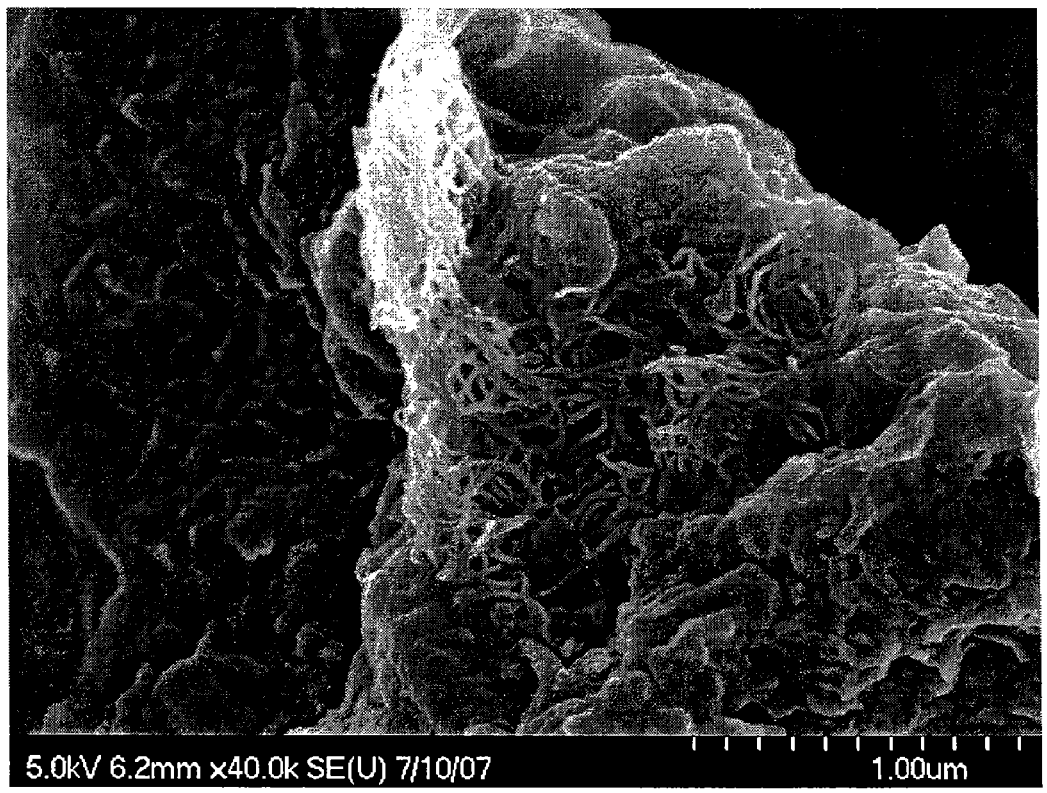
FIG. 5 is an SEM image of nylon 12 approximately 1% by weight of purified but non-functionalized MWNTs.
Figure 6:
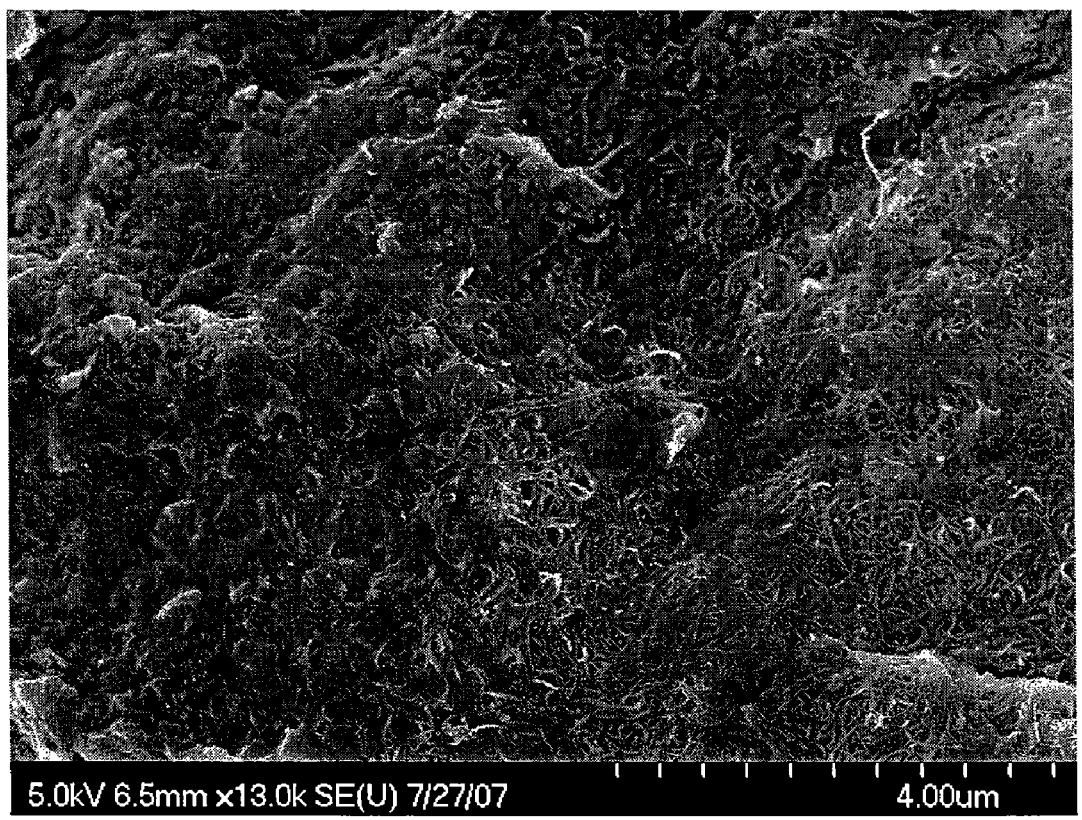
FIG. 6 is an SEM image of nylon 12 approximately 1% by weight of vinylanthracene-functionalized MWNTs.
Figure 7:
FIG. 7 is an SEM image of nylon 12 with approximately 1% by weight of vinylanthracene-functionalized MWNTs.

The nylon 12 polymer in FIGS. 4-8 was made by the in situ method described above. Purified MWNTs were added to the first batch at about 1% by weight, assuming a 100% yield of polymer. The second batch of nylon was made with the same percentage of MWNTs, however these tubes were functionalized with vinylanthracene. As shown in FIGS. 4 and 5, it is obvious that the non-functionalized tubes are collected in a single large clump which is surrounded entirely by polymer. However, the functionalized CNTs in the second batch appear in FIG. 6 to be dispersed throughout the polymer. At the 1 micron scale in FIG. 7, it is possible to see individual tubes separated from one another by nylon polymer.

Figure 8:
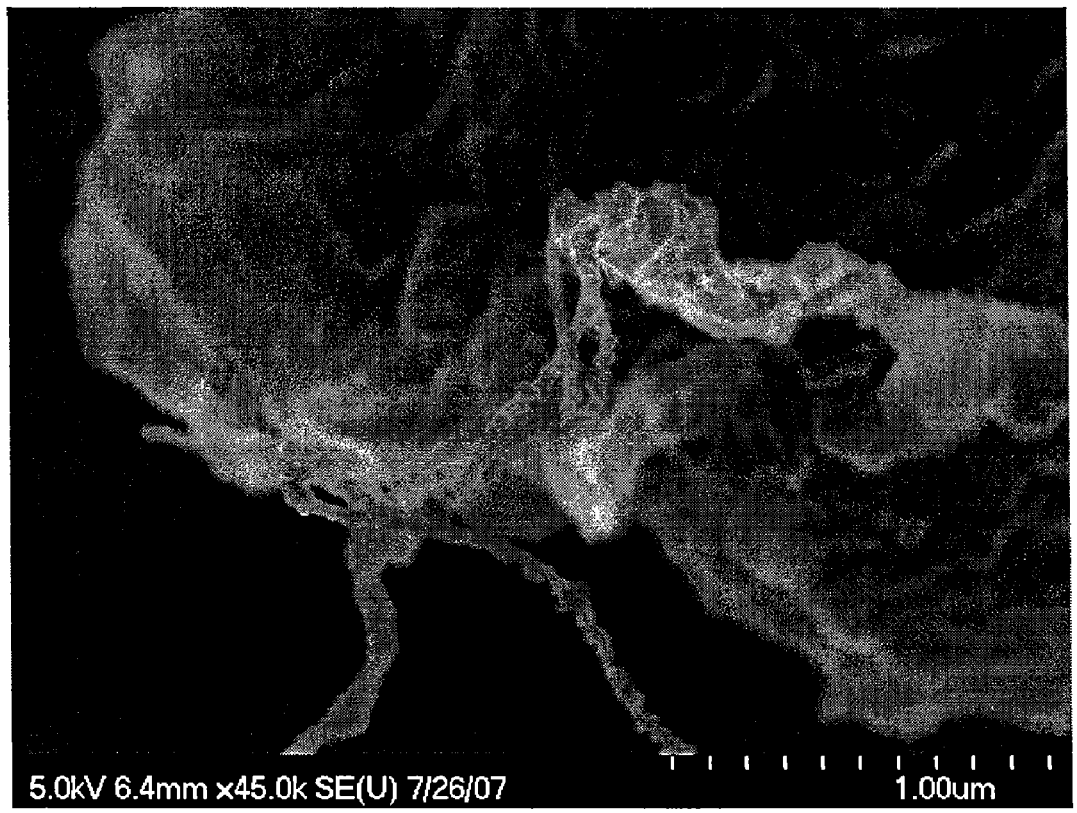
FIG. 8 is an SEM image of nylon 12 with approximately 1% by weight of vinylanthracene-functionalized MWNTs.

In the FIG. 8, there are small nodules of material that appear to be placed along the length of a long tube. This image indicates beads of nylon 12 growing at reactive sites along the CNT. The reactive sites can include defects in the CNT itself, including carboxylic acid sites, or non-covalently attached functional groups.

CNTs functionalized with vinylanthracene appear to aid in the dispersion of MWNTs through the nylon 12 polymer matrix. Though not directly involved in the chemical reaction between the amine and the dioyl chloride of the polymer, the vinyl group may interact with the polymer as well. The electron cloud surrounding the double bond of the vinyl group may share some electron density with the pi electrons in the amide link of the polymer. The location of the vinyl group, hanging off of the anthracene molecule with little steric interference from other bonds, may increase the likelihood that the CNT becomes entangled in the polymer matrix.

The polymerization of MWNTs with nylon 12 where the MWNTs have been functionalized with different anthracene derivatives is also possible. Candidates include diamino anthracene or dioyl chloride anthracene. In general, however, materials containing functionalized CNTs will see significant improvements due to improved dispersion and the chemical bonding between the polymer matrix and the nanotube itself.

As noted above, the chemical synthesis techniques of the present invention enable strong bonding between carbon nanotubes and polymers, resulting in polymer-nanotube composites with improved polymer properties. These properties include, but are not limited to, improved electrical conductivity, thermal conductivity, mechanical strength.

The polymer-nanotube composites of the present invention may be used, for example, as thermoplastics, thermosets and conductive fillers. These materials may, for example, be used to protect sensitive electronic devices against the threat of electrostatic discharge and electromagnetic or radio frequency (RF) interference. In addition, these materials may be used to create paint that is applied, for example, to the walls of homes, commercial properties, or automobile body parts. The polymer-nanotube composites of the present invention may be used to create electrostatic materials, electromagnetic shielding, active electronics, printed circuit boards or conducting adhesives The methods of the present invention may be used to create biocompatible carbon-nanotube polymers. The methods of the present invention may be used to create carbon-nanotube polymers that are incorporated into plastic chips, a wide variety of consumer products, or electronic devices. The methods of the present invention may be used to create carbon-nanotube polymers that are incorporated into rechargeable batteries, solid ectrolytes, electrical displays, photovoltaics, actuators, switches, sensors (for example, chemical, biochemical or thermal sensors), or smart structures.

The methods of the present invention may be used to create light weight, high strength structures. These structures may, for example, protect against radiation and particulates. Light weight, high strength structures created according to the methods of the present invention may be used, for example, to create vehicles, including aircraft and spacecraft, as well as sustaining habitation, hospitals, or other buildings on the moon, earth, or any other planet.

While various embodiments have been described above, it should be understood that they have been presented by way of example only, and not limitation. Thus, the breadth and scope of a preferred embodiment should not be limited by any of the above described exemplary embodiments, but should be defined only in accordance with the following claims and their equivalents.

What is claimed is:

1. A method for providing a polymerizable functionality to carbon nanotubes (CNTs), the method comprising the step of non-covalently bonding a polymerizable ligand to the CNTs, wherein the polymerizable ligand comprises a polyaromatic molecule with a polymerizable group attached thereto, and wherein the polymerizable group is selected from the group consisting of free vinyl group and free styryl group.

2. The method of claim 1, wherein the polyaromatic molecule comprises a polyaromatic hydrocarbon.

3. The method of claim 2, wherein the polyaromatic hydrocarbon comprises anthracene.

4. The method of claim 1, wherein the polymerizable group comprises a free styryl group.

5. The method of claim 1, wherein the polymerizable group comprises a free vinyl group.

6. The method of claim 1, wherein the polymerizable ligand comprises vinylanthracene.

7. The method of claim 1, wherein the polymerizable ligand is bonded to the sidewalls of the CNTs.

8. The method of claim 1, further comprising the step of covalently bonding the polymerizable ligand to the CNTs.

9. A method for providing a polymerizable functionality to carbon nanotubes (CNTs), the method comprising the step of non-covalently bonding vinylanthracene to the sidewalls of the CNTs.

10. A polymer-nanotube composite comprising:
carbon nanotubes (CNTs) functionalized by having a polymerizable ligand non-covalently bonded thereto; and
a polymer bound to the functionalized CNTs,
wherein the polymerizable ligand comprises a polyaromatic molecule with a polymerizable group attached thereto, and wherein the polymerizable group is selected from the group consisting of free vinyl group and free styryl group.

11. The polymer-nanotube composite as recited in claim 10, wherein the functionalized CNTs are dispersed throughout the polymer.

12. The polymer-nanotube composite as recited in claim 11, wherein the polymer is nylon.

13. The polymer-nanotube composite as recited in claim 10, wherein the polyaromatic molecule comprises a polyaromatic hydrocarbon.

14. The polymer-nanotube composite as recited in claim 13, wherein the polyaromatic hydrocarbon comprises anthracene.

15. The polymer-nanotube composite as recited in claim 10, wherein the polymerizable ligand comprises vinylanthracene.

16. The polymer-nanotube composite as recited in claim 10, wherein the polymerizable ligand is bonded to the sidewalls of the CNTs.

17. The polymer-nanotube composite as recited in claim 10, wherein the polymerizable ligand is also bonded covalently to the CNTs.

18. A polymer-nanotube composite comprising:
carbon nanotubes (CNTs) functionalized by having vinylanthracene non-covalently bonded to the sidewalls thereof; and
nylon bound to the functionalized CNTs.

* * * * *